(12) United States Patent
Solano Umaña et al.

(10) Patent No.: US 11,890,299 B2
(45) Date of Patent: Feb. 6, 2024

(54) ABLATION AGENT AND METHODS OF USE

(71) Applicant: HOLOGIC, INC., Marlborough, MA (US)

(72) Inventors: Victor Manuel Solano Umaña, Alajuela (CR); Estefania Alvarez, Watertown, MA (US)

(73) Assignee: Hologic, Inc., Marlborough, MA (US)

( * ) Notice: Subject to any disclaimer, the term of this patent is extended or adjusted under 35 U.S.C. 154(b) by 923 days.

(21) Appl. No.: 16/888,499

(22) Filed: May 29, 2020

(65) Prior Publication Data

US 2020/0405382 A1    Dec. 31, 2020

Related U.S. Application Data

(60) Provisional application No. 62/867,753, filed on Jun. 27, 2019.

(51) Int. Cl.
| | |
|---|---|
| *A61K 33/242* | (2019.01) |
| *A61K 9/00* | (2006.01) |
| *A61K 9/14* | (2006.01) |
| *A61M 21/00* | (2006.01) |
| *A61P 41/00* | (2006.01) |
| *A61B 18/00* | (2006.01) |
| *A61M 31/00* | (2006.01) |

(52) U.S. Cl.
CPC .......... *A61K 33/242* (2019.01); *A61K 9/0034* (2013.01); *A61K 9/14* (2013.01); *A61M 31/00* (2013.01); *A61P 41/00* (2018.01); *A61B 2018/0063* (2013.01); *A61B 2018/00559* (2013.01); *A61B 2018/00577* (2013.01); *A61B 2218/007* (2013.01); *A61M 2210/1433* (2013.01)

(58) Field of Classification Search
CPC ...... A61K 33/242; A61K 9/0034; A61K 9/14; A61M 31/00; A61M 2210/1433; A61P 41/00; A61B 2018/00559; A61B 2018/00577; A61B 2018/0063; A61B 2218/007
See application file for complete search history.

(56) References Cited

U.S. PATENT DOCUMENTS

| | | | |
|---|---|---|---|
| 4,766,226 A | 8/1988 | Hill et al. | |
| 6,087,493 A | 7/2000 | Wheelhouse et al. | |
| 8,741,384 B2 | 6/2014 | Maiorano et al. | |
| 9,579,403 B2 | 2/2017 | Yeh et al. | |
| 2004/0052729 A1 | 3/2004 | Penades et al. | |
| 2004/0063681 A1 | 4/2004 | Che | |
| 2006/0121079 A1 | 6/2006 | Danscher | |
| 2014/0012224 A1 | 1/2014 | Zhang et al. | |
| 2014/0086828 A1 | 3/2014 | Foster et al. | |
| 2016/0271274 A1 | 9/2016 | Ivkov et al. | |
| 2017/0209389 A1 | 7/2017 | Toth et al. | |
| 2018/0133446 A1* | 5/2018 | Shikhman | A61M 25/10 |

FOREIGN PATENT DOCUMENTS

| | | | | |
|---|---|---|---|---|
| WO | 2008063662 | | 5/2008 | |
| WO | WO-2008063662 A2 * | | 5/2008 | ........... A61K 33/242 |
| WO | 2008140624 | | 11/2008 | |
| WO | 2016057545 | | 4/2016 | |
| WO | WO-2016057545 A1 * | | 4/2016 | ......... A61B 18/1485 |

OTHER PUBLICATIONS

Summary of safety and Effectiveness Data (SSED). accessdata.fda. gov/cdrh_docs/pdf/P980040S124B.pdf (Year: 2001).*
Khan et al. (2019). Role of Per-Operative Wound Irrigation in Prophylaxis of Surgical Site Infection in Clean Contaminated Wounds. Pakistan Armed Forces Medical Journal, 69(1), 60-64. Retrieved from https://www.pafmj.org/index.php/PAFMJ/article/view/2497 (Year: 2019).*
Blum, D., "A Warning on Chemical Peels," The New York Times, Oct. 25, 2013.
Juhi, G., "Use of Tricholoroacetic for chemical ablation of endometrium in dysfunctional uterine bleeding," SAS Journal of Medicine, 1(3), ISSN 2454-5112, 82-85 (2015).
Hainfeld, J., et al. "Gold nanoparticles: A new x-ray contrast agent," The British Journal of Radiology, 79(939), 248-253 (2017).
Neuwirth, R., et al., "Evaluation of a silver nitrate endometrial ablation fluid delivery system as a chemical treatment for menorrhagia," Journal of Minimally Invasive Gynecology, 20(5), 627-630 (2013).
Wang, Y., et al., "Potent selective inhibition of MMP-14 by chloroauric acid and its inhibitory effect on cancer cell invasion," Royal Society of Chemistry Advances, 5, 17700-17708 (2014).

* cited by examiner

*Primary Examiner* — Jeffrey T. Palenik
*Assistant Examiner* — Janet Joseph
(74) *Attorney, Agent, or Firm* — Vista IP Law Group, LLP (57) ABSTRACT

A method of ablating a target body tissue, such as uterine endometrial lining tissue, includes applying an agent comprising $HAuCl_4$ to the target body tissue, wherein the $HAuCl_4$ has a molecular size greater than 50 microns, and removing the agent comprising $HAuCl_4$ from the target tissue after ablation of the target tissue begins.

18 Claims, 8 Drawing Sheets
(3 of 8 Drawing Sheet(s) Filed in Color)

| SAMPLE | CONCENTRATION | INJECTION VOLUME (ml) | TIME (min) | BOLUS SIZE (mm) |
|---|---|---|---|---|
| 1 |  |  |  | 17 |
| 2 | 1% | 1 | 2 | 14 |
| 3 |  |  |  | 16 |

COMPOUND DELIVERY

MEASUREMENT OF ABLATION PROFILE

ABLATION PROFILE WITHIN 1CM

ABLATION AGENT AND METHODS OF USE

RELATED APPLICATION DATA

This application claims the benefit of priority to provisional application Ser. No. 62/867,753, filed on Jun. 27, 2019.

FIELD OF INVENTION

The present disclosure relates generally to tissue ablation procedures. More particularly, the present disclosure relates to use of a chemical agent for performing endometrial ablation procedures.

BACKGROUND

A variety of devices and methods are currently available to treat abnormal uterine bleeding in women, which affects a significant number of patients (i.e., one in five women between 30-40 years old in the U.S.) and impacts their quality of life. A variety of treatment options are available, ranging from drug/hormones, contraception/IUD, minimally invasive treatments (e.g., thermal ablation, energy delivery devices, RF, chemical ablation and the like) and invasive treatments (e.g., hysterectomy surgery). Current trends are directed towards development and adoption of minimally invasive technologies, in order to preserve the patient's uterus, improve their quality of life, and minimize complications while reducing healthcare costs.

Endometrial ablation has become an outpatient medical procedure performed with local anesthesia using minimally invasive ablation devices that are designed to remove (e.g., thermally ablate) or otherwise destroy (change from living to necrotic) the endometrial lining of the uterus in women with abnormal uterine bleeding. Most of these procedures take 20 minutes or less, requiring lower skill, less equipment and a faster recovery than a traditional hysterectomy. These procedures can achieve amenorrhea rates ranging from 22% up to 72%, and success rates ranging from 67% to 93%, defined as normal or less bleeding levels.

However, some of the currently available procedures result in non-uniform and/or incomplete ablation of the endometrial lining, particularly procedures employing ablation devices that apply electrical current directly to the endometrial tissue, which increases the temperature of the tissue and causes moisture in the tissue to boil, thereby generating steam. The resulting ablation may not be uniform due to variations in electrical current density on the tissue surface and near the border of the electrodes. For example, high current densities at the electrode surface can lead to more ablation of the endometrial lining than desired. Currently employed ablation devices, typically inserted through a patient's cervix and then expanded within the uterus, can be difficult to properly position, limited adaptability for patient's anatomy (anteverted/retroverted) and deploy within a patient's uterus, which can lead to complications and potential injury to the patient.

Non-uniform ablation may make the evaluation of the uterine cavity more challenging, even weeks after the procedure. Non-uniform ablation may also create very dark, unrecognizable endometrium tissue which could mask cancer and/or abnormalities (fibroids or others) that were left intact or otherwise developed after the procedure. Necrotic ('brown cast' deep burn) tissue triggers significant scarring, atrophy and/or adhesions that form post thermal ablation treatment. Excessive scarring, adhesions, coagulation, protein denaturation and cell death that develops due to thermal necrosis tends to limit potential follow up evaluation through hysteroscopy weeks or years after the procedure. A follow up hysteroscopy procedure may be required if there is recurrent bleeding, risk of cancer, or if any other symptoms do not cease post treatment.

Existing methods for effecting thermal ablation of the endometrial lining tissue include circulation of heated fluid inside the uterus (either directly, or inside a balloon placed in the uterus), laser treatment of the lining, and resistive heating using application of RF energy to ablate the tissue. Newer technologies that use thermal based energy may create an ablation profile shallower than others, such as heating with water vapor or cryo-cooling. Recent ablation systems like AEGEA® and Channel MedSystems may also create a shallow ablation, due to their temperature profile and method of action but still they may not provide a complete ablation of the entire endometrium.

The application of caustic chemicals within the uterus is also known. For example, topical application of a saturated solution of zinc chloride to the uterine walls has been used to produce amenorrhea, sterility and to treat tumors. Use of caustic agents such as silver nitrate, zinc chloride and copper sulfate has been use in chemical ablation and sterilization. However, these caustic chemicals tend to easily migrate and spill out of the fallopian tubes, resulting in undesirable burns in the peritoneal cavity.

Some relatively recent clinical studies have tested topically applied trichloroacetic acid (TCA) for chemical endometrial ablation in patients with uterine bleeding, while comparing the advantages of pre-thinning the endometrium with danazol and goserelin acetate before ablation with TCA. Although TCA has been reported as a chemical endometrial ablation, a growing number of studies, mostly in laboratory animals, have suggested that TCA has troubling, more destructive effects. Recently, the International Agency on Cancer Research moved to classify it as a suspected human carcinogen. Evidence of carcinogenicity in animals, could indicate potential to cause harm in humans. A report published in the journal Environmental Science and Pollution Research found evidence of both genetic and cellular damage in human subjects (Blum, D. The New York Times, 2013).

Although application of chloroauric acid ($HAuCl_4$) is known to treat cancerous cells or for imaging, $HAuCl_4$ is not known to be used for endometrial ablation. U.S. Pat. Nos. 8,741,384 and 9,579,403, and International Publication WO2008063662 disclose the application of $HAuCl_4$ to treat cancerous cells, tumors or for imaging purposes, wherein nanoparticles of $HAuCl_4$ are used to penetrate tumors, cause cytotoxic reactions/apoptosis in cancerous cells, and/or being left behind for imaging due to their optical profile.

Thus, regardless of what kind of device and/or technology is used, endometrial ablation does not always provide adequate treatment of the entire endometrium. Some regions of the uterine cavity/endometrium are left without appropriate ablation, particularly areas that are difficult to reach and treat, for example uterine cornua and uteri with different shapes such as septum shape, T-shaped, and/or an extended transverse diameter. The limits of coverage of endometrial ablation are greatest when a device with a fixed configuration or geometry is used. The NovaSure™ device manufactured and sold by Hologic, Inc. (Marlborough, Mass.) overcomes this geometric limitation by applying suction during energy delivery in order to draw endometrial tissue into contact with its electrode array.

No currently available outpatient endometrial ablation device provides reliable long lasting clinically effective amenorrhea rates of more than 75%, while offering adaptability to the patient's anatomy to provide a complete coverage, and also delivering a short procedure with minimal pain and discomfort. There is a need to provide for more suitable endometrial ablation with a clinically effective disruptive ablation technology that is simple, cost effective, can provide complete coverage of the endometrium and adapts to a patient's anatomy, while also reducing pain and minimizing procedure time. Further, there is a need for an endometrial ablation procedure that is not temperature driven (lack of thermal necrosis) to avoid deep burns and excessive scarring, such that it would allow for effective hysteroscopy and other follow up procedures.

SUMMARY

In one embodiment of the disclosed inventions, a method of ablating a target body tissue includes applying an agent comprising $HAuCl_4$ to the target body tissue, wherein the $HAuCl_4$ has a molecular size greater than 50 microns. The agent may be provided in a fluid form, such as, without limitation, a gel, paste, or liquid solution. In one embodiment, the agent is provided in a saline solution.

In various embodiments, the $HAuCl_4$ agent is applied to the endometrial lining of a uterus by transcervically introducing the agent into the uterus, e.g., using a fluid injection apparatus. A sealing apparatus may be used to seal the cervix during introduction of the agent, wherein the fluid injection apparatus is configured to access the uterus through the sealing device. The method may further include sealing the uterine cornua prior to introduction of the agent into the uterus.

The agent is preferably removed from the target tissue after a desired amount of ablation of the target tissue has occurred, wherein the desired amount of ablation may be determined based on a concentration of the agent and an amount of elapsed time following the application of the agent to the target tissue. By way of example, in embodiments in which the target tissue is uterine endometrial lining tissue, removing the agent from the target tissue may be accomplished by washing the agent out of the uterus using a saline wash, which may be injected into the uterus and the combined agent and saline wash is simultaneously suctioned out of the uterus.

In one embodiment, a method of ablating the endometrial lining tissue of a uterus includes transcervically introducing a fluidic solution containing $HAuCl_4$ into the uterus, wherein the $HAuCl_4$ has a molecular size greater than 50 microns. The fluidic solution may be in a saline solution that is transcervically introduced into the uterus using a fluid injection apparatus. The method may include using a sealing apparatus to seal the cervix during introduction of the saline solution, wherein the fluid injection apparatus is configured to access the uterus through the sealing device. The method may also include sealing the uterine cornua prior to introduction of the fluidic solution into the uterus.

The $HAuCl_4$ is preferably removed (e.g., by using a saline wash) from the uterus after a desired amount of ablation of the endometrial lining tissue has occurred, wherein the desired amount of ablation of the endometrial lining tissue may be determined based on a concentration of the $HAuCl_4$ in the fluidic solution, and an amount of elapsed time following the introduction of the fluidic solution into the uterus. For example, a saline wash may be injected into the uterus, and the combined $HAuCl_4$ and saline wash is suctioned out of the uterus.

Other and further aspects and features of embodiments of the disclosed inventions will become apparent from the ensuing detailed description in view of the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions in differing embodiments are represented by like reference numerals throughout the figures. It should be understood that the figures are only intended to facilitate the description of the embodiments, and are not intended as an exhaustive description or limitation of the disclosed inventions, which are defined only by the appended claims and their equivalents.

In addition, an illustrated embodiment of the disclosed inventions need not show all aspects or advantages thereof. Further, an aspect or an advantage described in conjunction with a particular embodiment of the disclosed inventions is not necessarily limited to that embodiment and may be practiced in any other embodiments, even if not so illustrated or described herein.

Active Agent

In various embodiments of the disclosed inventions, an active agent comprising chloroauric acid ($HAuCl_4$) having particle size larger than 50 microns is used for chemical ablation of target tissue. In some embodiments, the active agent ($HAuCl_4$) is preferably mono dispersed and delivered in a fluid form, i.e., in a gel, paste, solution, compound, or the like, to the target tissue. In other embodiments, the active agent ($HAuCl_4$) may be delivered to the target tissue in any suitable form, such as, aqueous or oily suspensions, granules, powders, emulsions, capsules, pills, tables, syrups, elixirs or the like. In a preferred embodiment, the target tissue is one or more of: the endometrium, uterine lining, uterus cavity, and/or cervix. By way of non-limiting examples, the target tissue for application of the active agent ($HAuCl_4$) may be tissue of any other body organs or cavities, such as urinary bladder, kidney, lungs, bronchus, liver, pancreas, GI track organs, and the like.

It should be appreciated that the active agent ($HAuCl_4$) can be administered alone, or in combination with any ingredient(s), active or inactive, as long as the ingredient(s) do not neutralize the chemically denaturing and ablative effects of the active agent. The active agent ($HAuCl_4$) is hydrophilic (ionic), which can be diluted with purified water or other oxygen containing solvents, such as alcohols, esters, ethers, ketones or the like. In embodiments disclosed herein, the active agent ($HAuCl_4$) may be dissolved in DI-water at different concentrations from 0.1 to 1% mass/volume.

For example, a solid active agent ($HAuCl_4$) may be added to water at room temperature, and mixed for approximately ten (10) minutes, then filtered and ready to use. The active agent ($HAuCl_4$) solution may be stored for up to a year without stability issues. The hydrophilic nature of the solution facilitates the delivery and spread of the active agent ($HAuCl_4$) throughout the entire target tissue/cavity, while avoiding formation of lumps in the solution or patches of tissue without the solution when delivered. Exemplary tests show that delivering 0.5% of active agent ($HAuCl_4$) diluted in water into bovine liver (simulated tissue) with up to three (3) minutes of exposure, can achieve penetration depths in the tissue of 4-9 mm from the surface of the tissue.

Referring back to the desired particle size of the active agent ($HAuCl_4$) for chemical ablation, the particle size larger than 50 microns is relatively large compared to the active agent used for other applications, such as cytotoxic reactions, apoptosis in cancerous cells, and imaging, and it is also larger than actual mammal cell size. At 50 microns or less, the active agent ($HAuCl_4$) can still be engulfed by the macrophage as a foreign body response, even if the active agent ($HAuCl_4$) is not intended to be left behind in the target tissue after it has performed the chemical ablation.

In the process of denaturing the proteins, the tissue goes through an oxidation reaction and the gold particle within the active agent ($HAuCl_4$) compound is reduced, becoming an insoluble particle (byproduct) that remains in the tissue (e.g., endometrium) when the particle size is 50 microns or less. Significant presence of gold nanoparticles (byproduct) within the tissue would obscure potential follow up imaging (MRI), as these become MRI visible (high signal intensity, 'imaging contrast'), which could raise red flags in later follow up under MRI imaging, and mask cancer or other lesions.

Therefore, in embodiments of the disclosed inventions depicted and described herein, the particle size of the active agent ($HAuCl_4$) is larger than 50 microns, which allows the active agent ($HAuCl_4$) to avoid migration (e.g., stay within the target tissue of the uterine cavity), and being uniformly distributed in the target tissue (through for example, a syringe deposition). Further, the particle size (larger than 50 microns) of the active agent ($HAuCl_4$) allows for removal of the $HAuCl_4$ from the target tissue/cavity (flushing with saline, aspiration or other suitable techniques) due to the nature of the active agent ($HAuCl_4$). The active agent ($HAuCl_4$) can be delivered (e.g., administered, sprayed, injected, diffused, etc.) with any suitable device or medium (e.g., syringe, probe, catheter, etc.), and by any suitable route (e.g., local, topical, transdermal, subcutaneous, intramuscular, vaginal, rectal, etc.).

In one embodiment, the active agent ($HAuCl_4$) is reduced by the reaction with the uterus internal tissue/endometrial lining, causing chemical denaturing and necrosis of the endometrium (as cell membranes rupture and inflammatory tissue reaction occurs), leading to a fibrotic like response in the endometrium. However, no thermal necrosis, undesirable excessive scarring, acute phase necrotic coagulation, atrophy, partial adhesions, obliteration of the uterine cavity, protein denaturation, cell death or apoptosis is caused by the application of the active agent ($HAuCl_4$) within the uterus. Thus, an advantage of the chemical ablation produced by the active agent ($HAuCl_4$) is the lack of thermal necrosis as the ablation is not temperature driven; such that the active agent ($HAuCl_4$) produces less scarring and less pain when applied and removed (e.g., washed out). Further, the active agent ($HAuCl_4$) has the described ablative properties and its reaction product (metallic gold) does not have undesirable toxic effects in tissue.

Figure 1A:
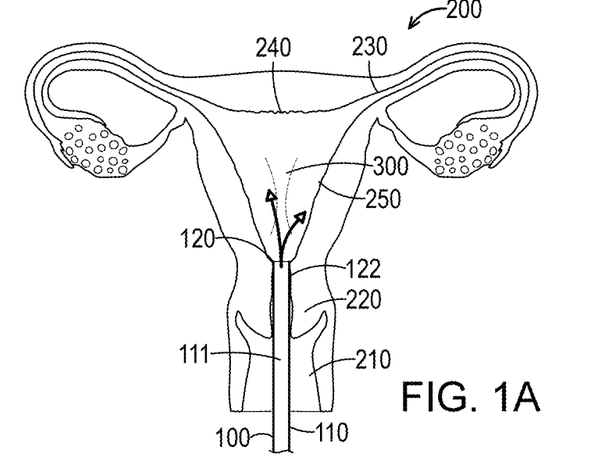
FIGS. 1A-C are cross-sectional views of an exemplary method of using the active agent according to embodiments of the disclosed inventions.
Figure 1B:
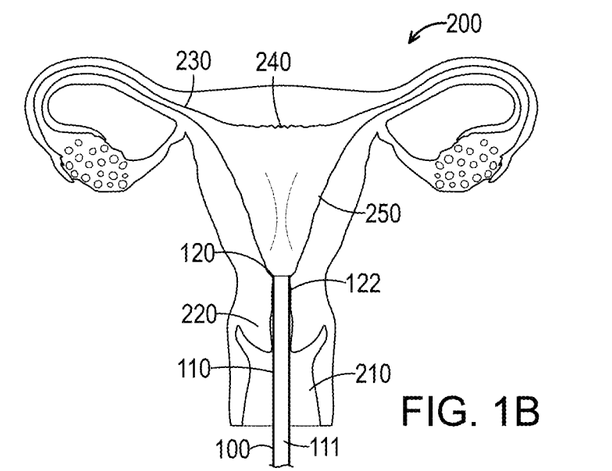
Figure 1C:
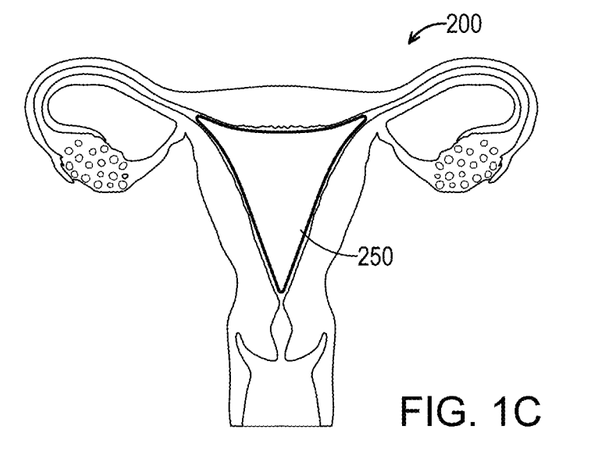

FIGS. 1A-C illustrate an exemplary method of use of the active agent ($HAuCl_4$) 300 for treatment of a uterine cavity in a patient. A delivery system 100 having an elongated member 110 is used to deliver the active agent ($HAuCl_4$) 300 into the uterus 200, the elongated member having a proximal end (not shown) and a distal end 122 and a lumen 111 therebetween. The elongated member 110 is advanced through the vagina 210 and cervix 220 to gain access to the uterus 200. In FIGS. 1A-B, the delivery system 100 having the elongated member 110 comprises an outer diameter smaller than 3 mm, minimizing dilation of the cervix 220 and reducing patient discomfort. The distal end 122 of the elongated member 110 of the delivery system 100 has a blunt tip to facilitate atraumatic insertion through the cervix 220, and may have a marker or other suitable radiopaque feature (not shown) for imaging purposes. In some embodiments, the distal end 122 of the elongate member 110 may be pre-bent, or having an articulated distal end or the like (not shown), with suitable angles (freedom of movement) to facilitate delivery of the active agent ($HAuCl_4$) to some areas of the uterus 200, for example, the cornua 230.

The elongated member 110 defines a lumen 111 in fluid communication with a distal opening 120 for delivery of the active agent ($HAuCl_4$) within the uterus 200. In some embodiments, after the elongated member 110 of the delivery system 100 is inserted through the cervix 220, the elongated member 110 is further advanced until the distal end 122 contacts the fundus 240 of the uterus 200. Then, the active agent ($HAuCl_4$) is delivered within the uterus 200 out of the distal opening 120 of the elongated member 100, while the elongated member 110 is withdrawn, thus covering substantially all the endometrium 250 with the active agent ($HAuCl_4$). In other embodiments, the active agent ($HAuCl_4$) is delivered out of the distal opening 120 of the elongated member 100 while the distal end 122 is distally disposed from the cervix 220, as shown in FIG. 1A.

The delivery of the active agent ($HAuCl_4$) into the uterus 200 could be performed with the assistance of ultrasound and/or hysteroscopy guidance, similar to known endometrial biopsy or embryo transfer procedures performed with visualization. The distal end 122 of the elongated member 110 of the delivery system 100 may include radiopaque or echogenic features (not shown) and since the active agent ($HAuCl_4$) comprises a hypoechoic nature, delivery of the active agent ($HAuCl_4$) can be seen under ultrasound as scattering when the $HAuCl_4$ is delivered within the uterus 200.

In some embodiments, a cervical seal (e.g., expandable member, balloon or polymeric annular member coupled to the delivery system 100) may be used to prevent leakage or spilling of the active agent ($HAuCl_4$) during the ablation procedure. Additionally, the uterine cornuas 230 can be sealed with a hydrogel or polymer prior delivery of the active agent ($HAuCl_4$) in order to prevent any spilling of the $HAuCl_4$ into fallopian tubes. In such embodiments employing a cervical seal, some fluid (e.g., saline, air, etc.) may be delivered into the uterus 200 prior delivery of the active agent ($HAuCl_4$) in order to confirm the uterus is intact (not perforated) prior ablation. Additionally or alternatively, a vacuum check can be performed prior delivery of the active agent ($HAuCl_4$) to confirm that the $HAuCl_4$ will not leak outside the uterus 200.

The active agent ($HAuCl_4$) may be delivered into the patient's uterus 200 with or without an analgesia in an office setting, as an ambulatory, outpatient procedure. The active agent ($HAuCl_4$) may be delivered in a fluid form, such as a gel, paste, liquid solution or the like. The active agent ($HAuCl_4$) may be preloaded within the delivery system 100 (e.g., catheter, syringe). Alternatively, the active agent ($HAuCl_4$) may be disposed in a pre-packaged vial detachably coupled to the delivery system 100. When delivered within the uterus 200, the active agent ($HAuCl_4$) contacts and penetrates the endometrium lining causing chemical ablation of the endometrium. Chemical ablation is based on cytoplasmic dehydration and cellular protein denaturation that leads to direct cellular necrosis, and relies on toxicity of the $HAuCl_4$ to produce necrosis of the endometrium, without raising or increasing tissue temperature to reach protein denaturation and cell death.

Other variations of the delivery system 100 suitable for delivery of the active agent ($HAuCl_4$) in a uterus may be contemplated. By way of example, the delivery system 100 can have a variety of configurations, such as a catheter, syringe, probe, or the like.

Referring back to FIG. 1A, when the distal opening 120 of the delivery system 100 is disposed within the uterus 200, the active agent ($HAuCl_4$) 300 is advanced through the lumen 111 of elongated member 110 and delivered out of the distal opening 120 of the delivery system 100 into the uterus 200 (FIG. 1A). The delivered active agent ($HAuCl_4$) 300 contacts and covers the uterine cavity, chemically denaturing and ablating the endometrium. The active agent ($HAuCl_4$) covers or substantially covers the entire uterine cavity when delivered. Denature and ablation of the endometrium with the active agent ($HAuCl_4$) takes approximately three (3) minutes or less (preferably less than two minutes) with penetration depths in a rage of 4-9 mm from the surface of the endometrium 250.

The delivery system 100 may be coupled to an injection/suction source(s) (not shown), so that once the desired amount of tissue ablation is complete (approx. 2 minutes or less), the delivery system 100 may inject a saline solution to remove (i.e., wash out) the active agent ($HAuCl_4$) from the endometrial tissue, while simultaneously suctioning the resulting saline/$HAuCl_4$ out of the uterus 200 (FIG. 1B). Since the chemical ablation would otherwise continue until the active agent ($HAuCl_4$) is removed from the tissue, flushing/washing out the cavity with saline (e.g., 5 cc or more) is needed in order to cease the ablation process. Flushing the uterus 200 may be performed by the delivery system 100 or any other suitable device, such as a multilumen delivery system (not shown), that can deliver saline transcervically while suctioning (vacuum) to remove the active agent ($HAuCl_4$) and ablated/necrotic tissue. The vacuum could be constant, using a vacuum pump or using a device that has intermittent vacuum which with every pump/pressed trigger, the inner mechanism can create vacuum to aspirate the fluid back to an external container (not shown).

In some embodiments, several cc of saline will be introduced and immediately removed from the uterus 200, in a washing cycle of three times using a pump and vacuum system. As the amount of active agent ($HAuCl_4$) is preferably pre-measured/pre-defined (e.g., by the delivery device manufacturer) to achieve a suitable endometrial ablation and penetration profile within a two (2) minute procedure, a pre-determined amount of saline should be available to the operator in order to adequately flush the uterus 200 once the ablation process is complete. Alternative or additionally, a neutralizing base may be delivered into the uterus 200 to neutralize the ablation of the endometrium by the active agent ($HAuCl_4$). Therefore, the active agent ($HAuCl_4$) is removed from the uterus 200. The chemical ablation is completed as shown in FIG. 1C and the endometrium 250 is ablated. In some embodiments, an endoscopy probe, a chip camera coupled to the delivery system 100, or other type of visualization device may be introduced into the uterus 200 to confirm that the ablation has been completed.

Figure 2A:
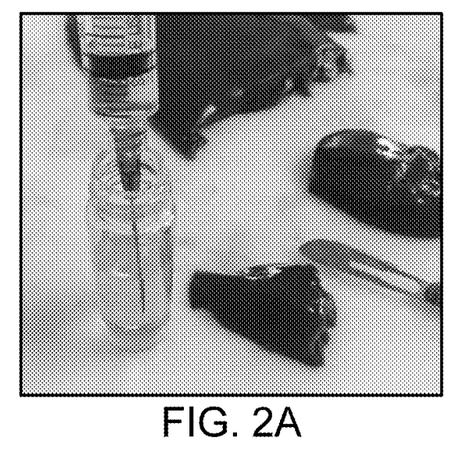
FIGS. 2A-C are perspective views of the effects of the active agent according to embodiments of the disclosed inventions.
Figure 2B:
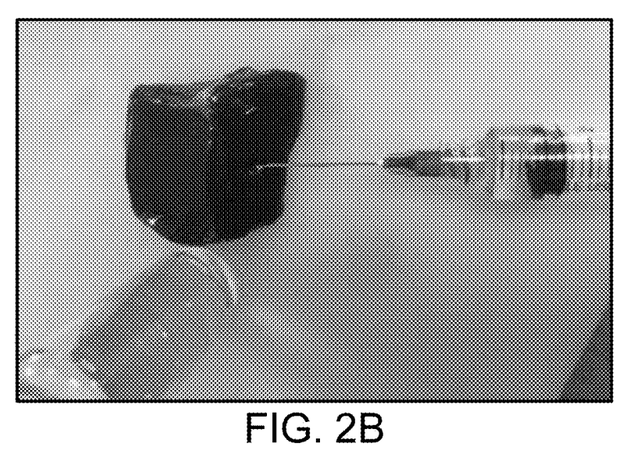
Figure 2C:
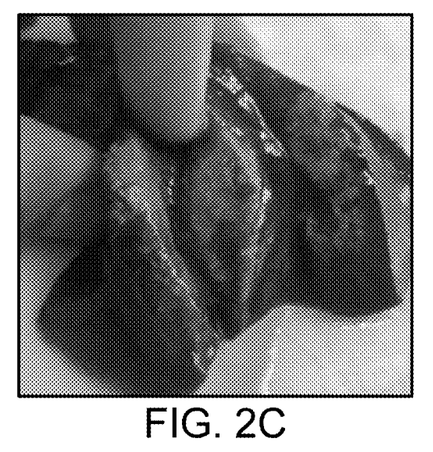

FIGS. 2A-C and FIGS. 3-5 illustrate exemplary ablative effects of the active agent ($HAuCl_4$) 300 when applied to a sample tissue. FIG. 2A illustrates a liquid DI water solution of active agent ($HAuCl_4$) 300, a syringe 400 and a sample bovine liver tissue 500. FIG. 2B show that delivering of the active agent ($HAuCl_4$) 300 diluted in water into tissue 500 by injection via syringe 400. FIG. 2C depicts the ablated tissue 500.

Figure 3:
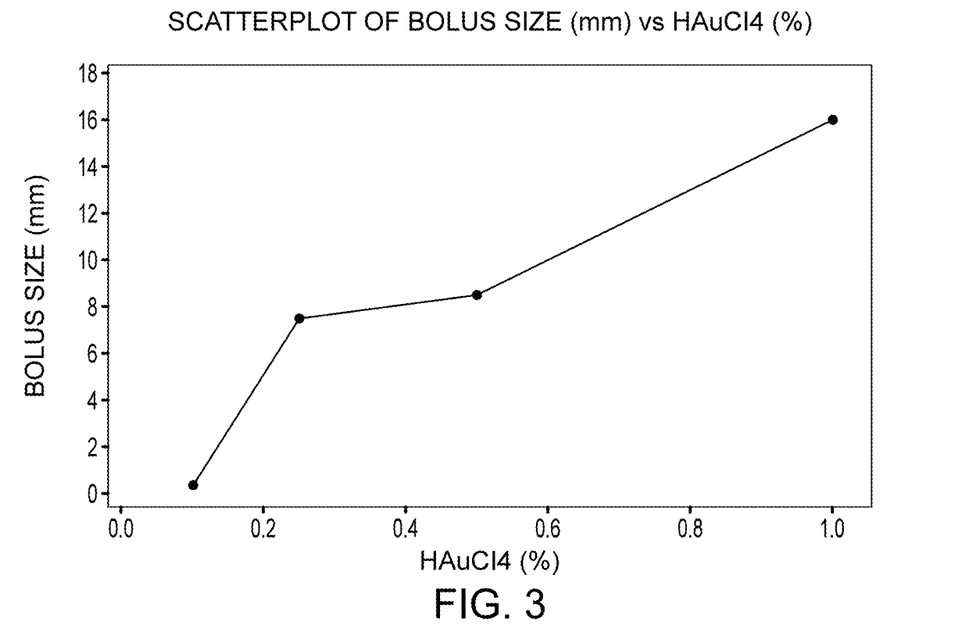
FIGS. 3 and 4 are data charts of the active agent effects on tissue according to embodiments of the disclosed inventions.

Various tests were performed in sample tissue 500. For example, in some tests the active agent ($HAuCl_4$) 300 (1 ml) was delivered into the tissue 500 having a constant time of exposure (e.g., 2 minutes at room temperature) but the bolus size (ablated volume) was measured under different active agent ($HAuCl_4$) concentrations (FIG. 3). Data contained in FIG. 3 was measured three times and obtained the average value for the graph, as shown. As known in the art, bolus tests are common to understand diffusion and effectiveness of ablative technologies.

Figure 4:
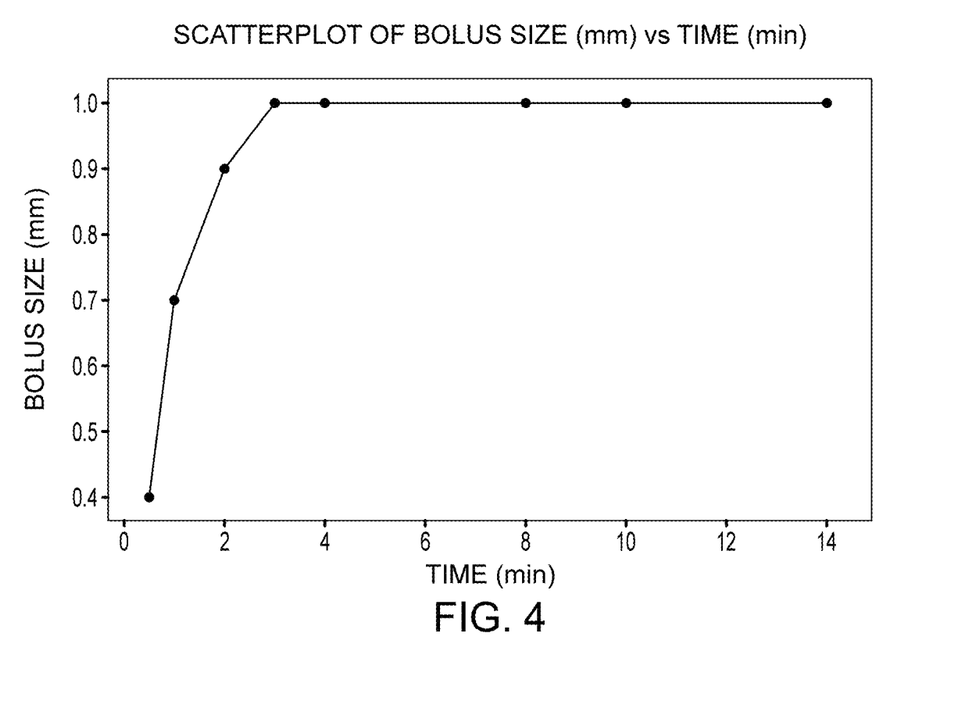

In another test, the active agent ($HAuCl_4$) concentration was maintained constant at 0.5% in an injected 1 ml into the sample tissue but the bolus size was measured at different times (FIG. 4). Data reference in FIG. 4 was measured five times and obtained the average value for the graph, as shown. The bolus size increases with the active agent ($HAuCl_4$) concentration, as the $HAuCl_4$ is more concentrated, the ablation of the tissue is stronger and deeper.

Additionally, the bolus size is time dependent but after 3 minutes, 1 ml of 0.5% $HAuCl_4$ DI-water solution stopped the reaction because the solution is not strong enough to penetrate the tissue further. Therefore, the active agent ($HAuCl_4$) chemical ablation is quantity and time dependent.

Figure 5:
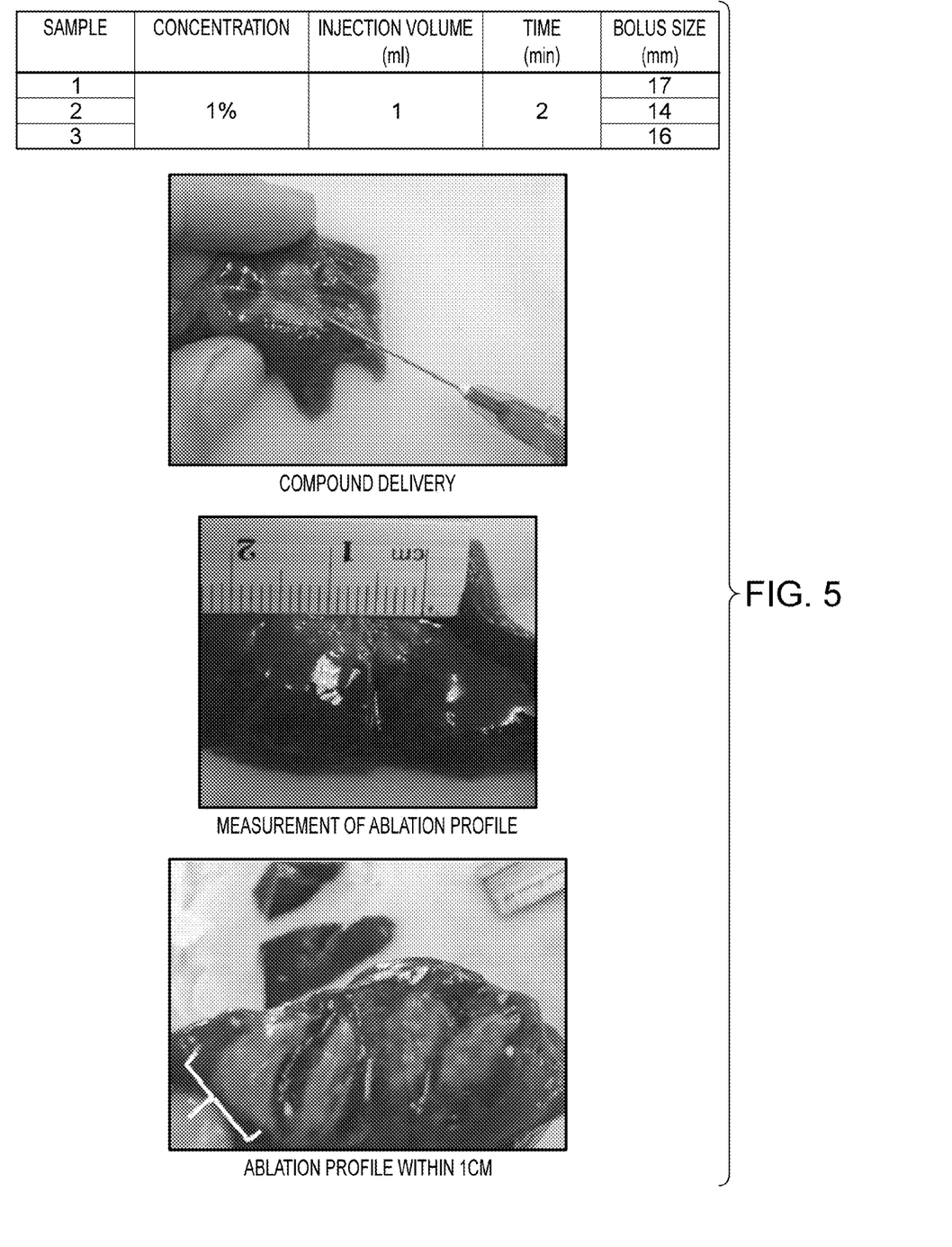
FIG. 5 is a data chart and ablated tissue of the active agent effects, according to other embodiments of the disclosed inventions.

FIG. 5 illustrates sample tissue ablation profiles measured and characterized for a range of active agent ($HAuCl_4$) concentration (0.10%, 0.25% and 1% of HAuCl4 within 2 minutes, and a variety of bolus sizes). Optimization was performed to select 0.5% of $HAuCl_4$ in order to achieve desirable ablation profile (rage of 4-9 mm ablation depth of tissue). Additional optimization could be performed to achieve shallower profiles (if desired).

Figure 6A:
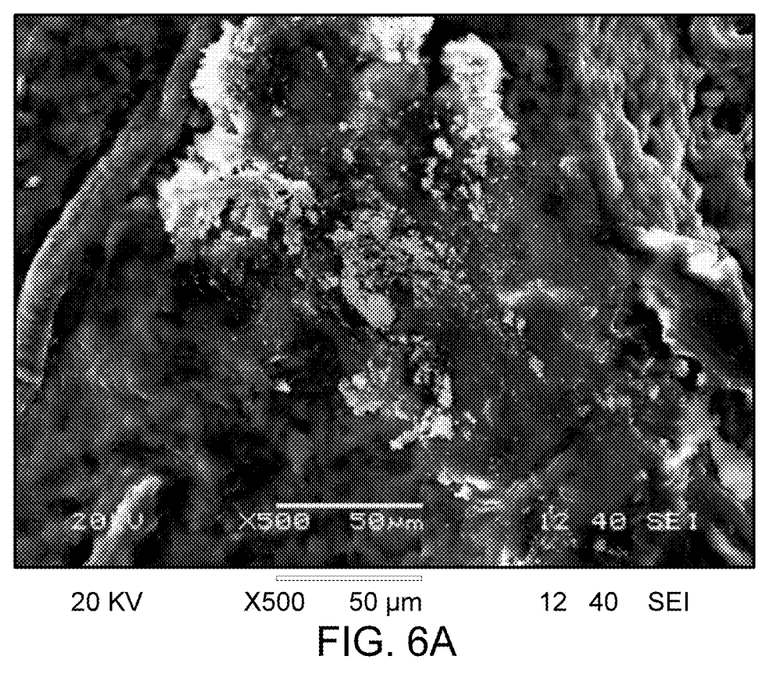
FIGS. 6A-C are cross-sectional views ablated tissue using the active agent, according to embodiments of the disclosed inventions.
Figure 6B:
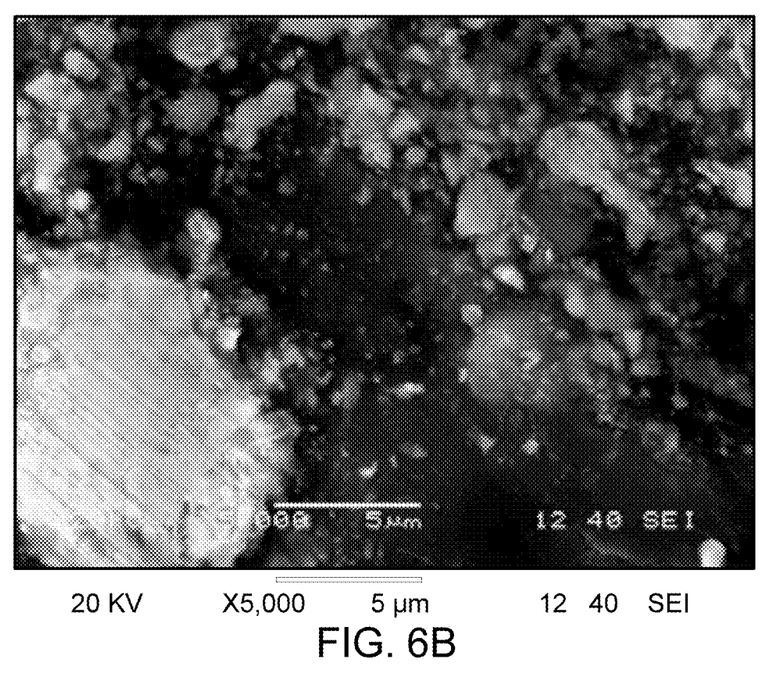
Figure 6C:
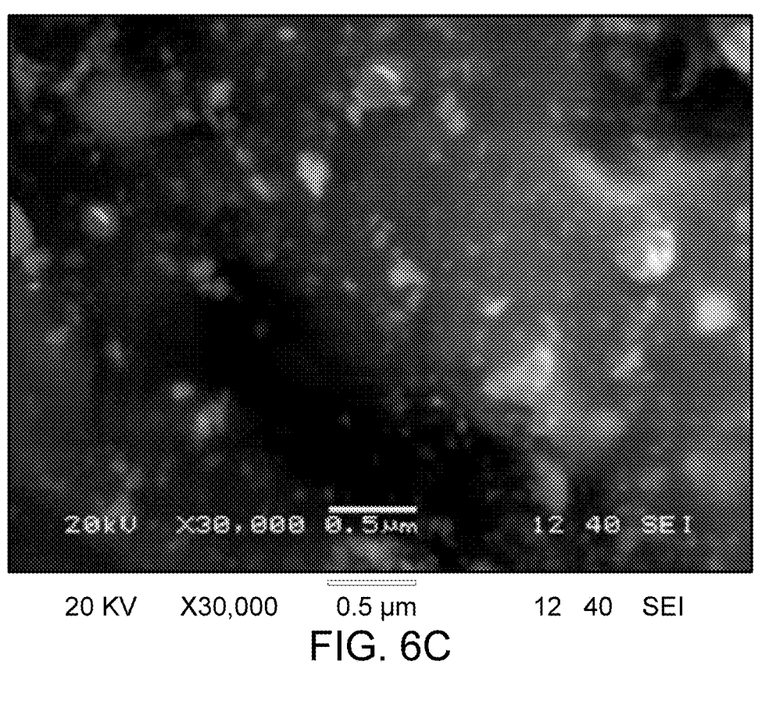

FIGS. 6A-C illustrate exemplary ablative effects of the active agent ($HAuCl_4$) 300 in sample tissue, including particle characterization through microscopy. Post ablated liver sample tissue was dehydrated and inspected under a scanning electron microscope (SEM). The obtained micrographs from the liver's cross-section shows an agglomeration of gold particles and the main portion of these shows a particle size in the range of micrometers. FIG. 6A is a cross-section of the ablated tissue at ×500 magnification, FIG. 6B is at ×5000 magnification and FIG. 6C is at ×30000 magnification. The ablation process is an oxidation reaction where the tissue or organic material is oxidized and the gold is reduced. The main portion of these particles show a size in the range of micrometers (5 to 50 microns).

Figure 7:
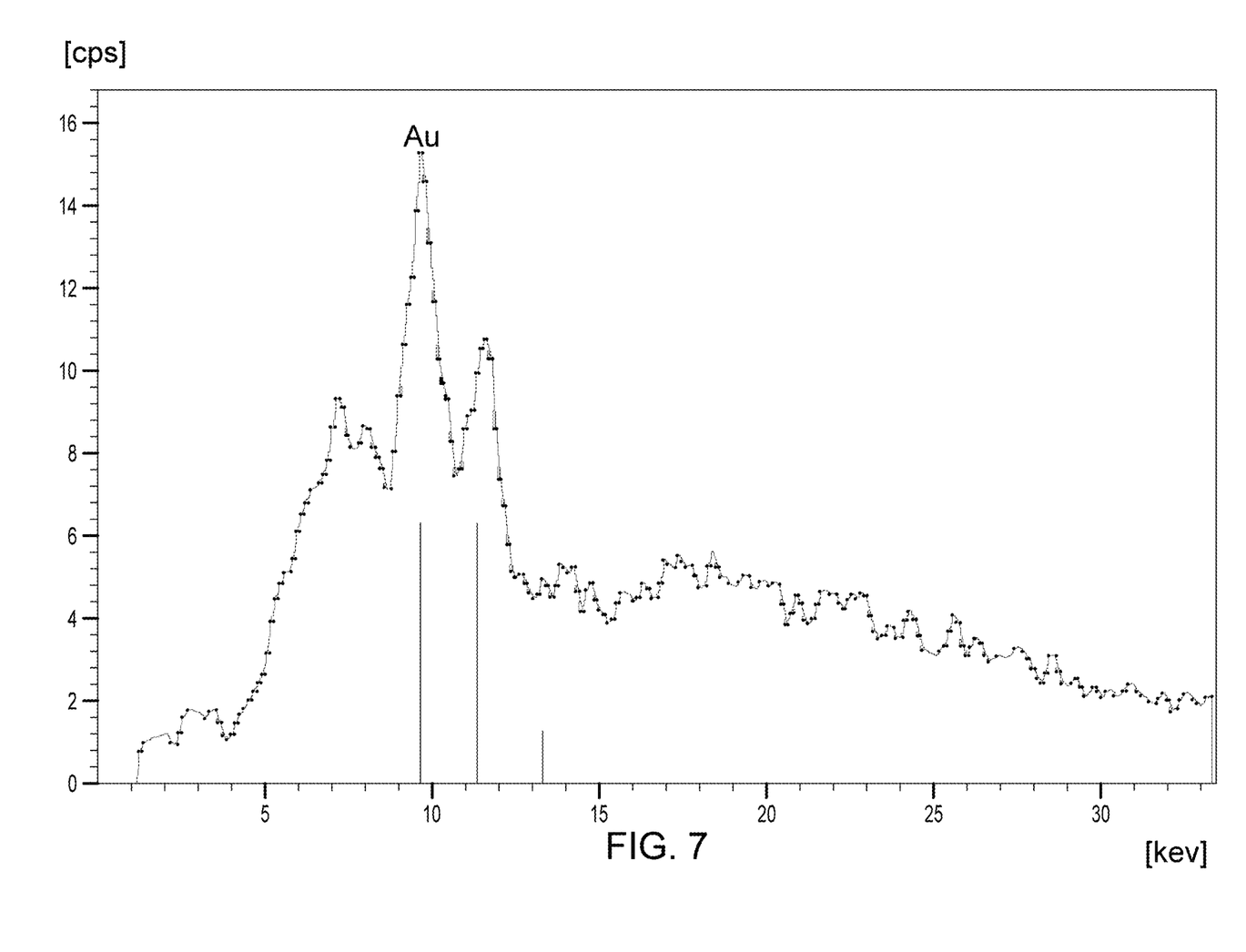
FIG. 7 is another data chart of the active agent effects on tissue according to embodiments of the disclosed inventions.

FIG. 7 illustrates gold presence on tissue after chemical ablation, matching the results observed in embodiments of FIGS. 6A-C. FIG. 7 is an X-ray flouorescent (XRF) spectrum from the liver tissue cross-section after chemical ablation of the embodiments of FIGS. 6A-C occurred.

Figure 8:
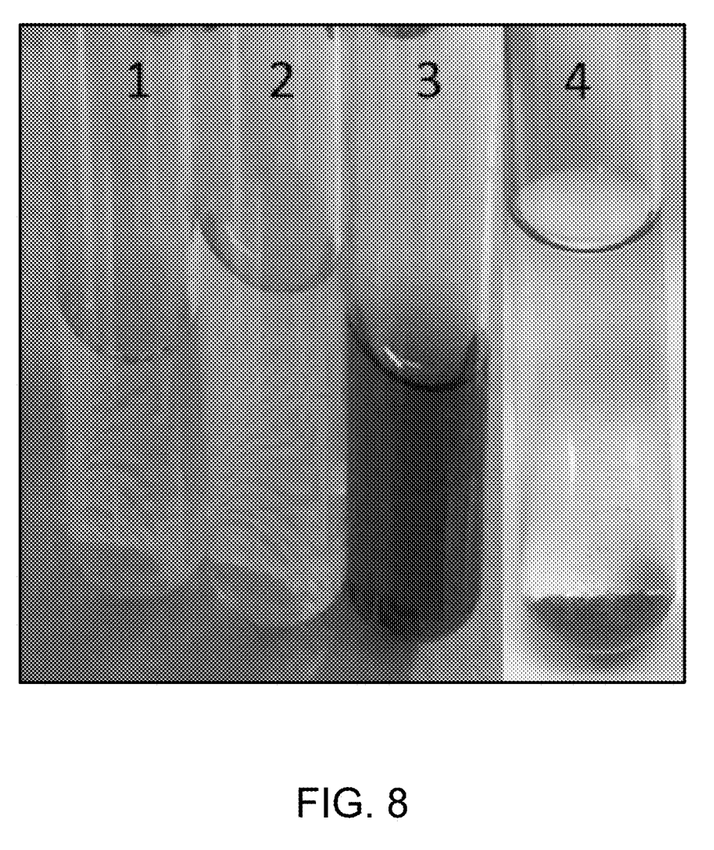
FIG. 8 is a perspective view of an exemplary neutralization of the active agent according to embodiments of the disclosed inventions.

FIG. 8 illustrates an exemplary method to neutralize the active agent ($HAuCl_4$) according to embodiments of the invention. The remaining active agent ($HAuCl_4$) within the tissue/cavity may be neutralized with $NaCO_3$ 5% mass/volume solution. With a ratio 1:1, steps 1-2-3 and 4 of FIG. 8 show the neutralization process. The byproduct is shown at the bottom of the test tube at step 4 of FIG. 8, which could be removed by flushing/suction and collected in an external collection system (not shown).

Although particular embodiments have been shown and described, it will be understood that they are not intended to limit the disclosed inventions. The specification and drawings are, accordingly, to be regarded in an illustrative rather than restrictive sense.

What is claimed is:

1. A method of ablating a target body tissue, comprising:
    applying an agent comprising $HAuCl_4$ to the target body tissue, wherein the $HAuCl_4$ has a molecular size greater than 50 microns, and
    removing the agent from the target tissue after ablation of the target tissue begins.

2. The method of claim 1, wherein the agent is in a fluid form.

3. The method of claim 2, wherein the agent is in a gel, paste, or liquid solution.

4. The method of claim 2, wherein the agent is in a saline solution.

5. The method of claim 1, wherein the target body tissue is the endometrial lining of a uterus.

6. The method of claim 5, wherein applying the agent to the target body tissue comprises transcervically introducing the agent into the uterus.

7. The method of claim 6, wherein the agent is transcervically introduced into the uterus using a fluid injection apparatus.

8. The method of claim 7, further comprising using a sealing apparatus to seal the cervix during introduction of the agent, wherein the fluid injection apparatus is configured to access the uterus through the sealing device.

9. The method of claim 7, further comprising sealing the uterine cornua prior to introduction of the agent into the uterus.

10. The method of claim 1, wherein the ablation is determined based on a concentration of the agent and an amount of elapsed time following the application of the agent to the target tissue.

11. The method of claim 1, wherein the target tissue comprises uterine endometrial lining tissue, and wherein removing the agent from the target tissue comprises washing the agent out of the uterus using a saline wash.

12. The method of claim 11, wherein the saline wash is injected into the uterus and the combined agent and saline wash is simultaneously suctioned out of the uterus.

13. A method of ablating the endometrial lining tissue of a uterus, the method comprising:
    transcervically introducing a fluidic solution containing $HAuCl_4$ into the uterus, wherein the $HAuCl_4$ has a molecular size greater than 50 microns, and
    removing the $HAuCl_4$ from the uterus after ablation of the endometrial lining tissue begins.

14. The method of claim 13, wherein the fluidic solution is in a saline solution, and wherein the saline solution is transcervically introduced into the uterus using a fluid injection apparatus.

15. The method of claim 13, further comprising using a sealing apparatus to seal the cervix during introduction of the saline solution, wherein the fluid injection apparatus is configured to access the uterus through the sealing device.

16. The method of claim 13, further comprising sealing the uterine cornua prior to introduction of the fluidic solution into the uterus.

17. The method of claim 13, wherein the ablation of the endometrial lining tissue is determined based on a concentration of the $HAuCl_4$ in the fluidic solution, and an amount of elapsed time following the introduction of the fluidic solution into the uterus.

18. The method of claim 13, wherein removing the $HAuCl_4$ from the uterus comprises washing the $HAuCl_4$ out of the uterus using a saline wash, wherein the saline wash is injected into the uterus and the combined $HAuCl_4$ and saline wash is suctioned out of the uterus.

* * * * *